(12) United States Patent
Vendrely et al.

(10) Patent No.: US 8,394,105 B2
(45) Date of Patent: Mar. 12, 2013

(54) APPARATUS FOR DISPENSING BONE CEMENT

(75) Inventors: Timothy G. Vendrely, Fort Wayne, IN (US); Michael Kryger, Winnipeg (CA)

(73) Assignee: DePuy Synthes Products, LLC, Warsaw, IN (US)

( * ) Notice: Subject to any disclaimer, the term of this patent is extended or adjusted under 35 U.S.C. 154(b) by 1739 days.

(21) Appl. No.: 11/375,484

(22) Filed: Mar. 14, 2006

(65) Prior Publication Data

US 2007/0233147 A1    Oct. 4, 2007

(51) Int. Cl.
A61F 2/00    (2006.01)

(52) U.S. Cl. ............................................ 606/92; 606/94

(58) Field of Classification Search ............. 606/92, 606/93, 94, 95; 604/31, 65, 111, 82, 83, 604/84, 85, 86, 87, 88, 89, 90, 91, 92, 207, 604/208, 209, 210, 211; 433/80, 89, 90; 439/476.1, 477–484; 600/393, 394, 372; 204/205, 408

See application file for complete search history.

(56) References Cited

U.S. PATENT DOCUMENTS

| | | | |
|---|---|---|---|
| 2,469,736 A | | 5/1949 | McBrayer |
| 3,000,805 A | * | 9/1961 | Carritt et al. ................. 204/408 |
| 3,144,966 A | | 8/1964 | Cook |
| 3,413,595 A | | 11/1968 | Babikov et al. |
| 3,816,811 A | * | 6/1974 | Cmelik K. .................... 324/667 |
| 4,278,934 A | | 7/1981 | Ihara et al. |
| 4,327,587 A | | 5/1982 | Docekal et al. |
| 4,338,925 A | | 7/1982 | Miller |
| 4,405,249 A | * | 9/1983 | Scales .......................... 401/182 |
| 4,461,407 A | | 7/1984 | Finnegan |
| 4,546,312 A | | 10/1985 | Brun et al. |
| 4,546,767 A | | 10/1985 | Smith |
| 4,559,810 A | | 12/1985 | Hinrichs et al. |
| 4,671,263 A | | 6/1987 | Draenert |
| 4,680,958 A | | 7/1987 | Ruelle et al. |
| 4,854,716 A | | 8/1989 | Ziemann et al. |
| 4,862,384 A | | 8/1989 | Bujard |
| 4,888,818 A | | 12/1989 | Schmitt et al. |
| 4,921,415 A | | 5/1990 | Thomas, III et al. |
| 4,994,065 A | | 2/1991 | Gibbs et al. |

(Continued)

FOREIGN PATENT DOCUMENTS

| | | |
|---|---|---|
| DE | 2413818 A1 | 10/1975 |
| DE | 2627904 A1 | 1/1978 |

(Continued)

OTHER PUBLICATIONS

English Translation of DE10008481 A1.*

(Continued)

*Primary Examiner* — Jan Christopher Merene
(74) *Attorney, Agent, or Firm* — Barnes & Thornburg LLP

(57) ABSTRACT

An apparatus for dispensing bone cement includes a cartridge for containing the bone cement. The apparatus also includes a plunger insertable into the cartridge. An impedance sensor is coupled to the plunger and configured to produce an output signal indicative of an impedance of bone cement contained in the cartridge. The apparatus may also include a processing circuit configured to determine an impedance value of bone cement contained within the cartridge based on the sensor signal. The processing circuit may activate a visual indicator based on the impedance value to indicate that the dough time, the end-of-work time, and/or setting-time of bone cement contained in the cartridge has been reached.

24 Claims, 7 Drawing Sheets

U.S. PATENT DOCUMENTS

| | | | |
|---|---|---|---|
| 5,181,636 A | 1/1993 | Anderson et al. | |
| 5,187,980 A | 2/1993 | Blair et al. | |
| 5,431,654 A | 7/1995 | Nic | |
| 5,501,374 A | 3/1996 | Laufer et al. | |
| 5,556,009 A | 9/1996 | Motzko | |
| 5,585,733 A * | 12/1996 | Paglione | 324/678 |
| 5,638,997 A | 6/1997 | Hawkins et al. | |
| 5,829,875 A | 11/1998 | Hagel et al. | |
| 5,893,488 A | 4/1999 | Hoag et al. | |
| 6,020,396 A | 2/2000 | Jacobs | |
| 6,023,170 A | 2/2000 | Hilhorst et al. | |
| 6,045,555 A | 4/2000 | Smith et al. | |
| 6,086,594 A | 7/2000 | Brown | |
| 6,155,463 A | 12/2000 | Dentler | |
| 6,161,731 A * | 12/2000 | Sigg | 222/158 |
| 6,227,040 B1 | 5/2001 | Hastings et al. | |
| 6,296,149 B1 | 10/2001 | Long | |
| 6,491,635 B1 | 12/2002 | Mazess et al. | |
| 6,644,122 B2 | 11/2003 | Borowezak et al. | |
| 6,702,784 B1 * | 3/2004 | Sheckler et al. | 604/181 |
| 6,736,537 B2 | 5/2004 | Coffeen et al. | |
| 6,854,349 B2 | 2/2005 | Brandhorst et al. | |
| 2003/0176807 A1 | 9/2003 | Goetz et al. | |
| 2004/0024410 A1* | 2/2004 | Olson et al. | 606/93 |
| 2004/0267272 A1 | 12/2004 | Henniges et al. | |
| 2005/0048886 A1 | 3/2005 | Mercuri | |
| 2005/0105384 A1 | 5/2005 | Eder et al. | |
| 2005/0105385 A1 | 5/2005 | McGill et al. | |
| 2005/0119660 A1 | 6/2005 | Bourlion et al. | |
| 2006/0000284 A1 | 1/2006 | Sherman et al. | |
| 2006/0122623 A1* | 6/2006 | Truckai et al. | 606/94 |
| 2007/0154874 A1* | 7/2007 | Sherman et al. | 434/262 |
| 2008/0269761 A1 | 10/2008 | Truckai et al. | |

FOREIGN PATENT DOCUMENTS

| | | |
|---|---|---|
| DE | 4120573 | 12/1992 |
| DE | 10008481 A1 | 9/2001 |
| EP | 0995981 A2 | 4/2000 |
| FR | 1316494 | 2/1963 |
| JP | 63138249 | 6/1988 |
| WO | 9610173 | 4/1996 |
| WO | 2004014262 | 2/2004 |
| WO | 2005048886 | 6/2005 |
| WO | WO 2005/048867 A2 | 6/2005 |
| WO | WO 2005/048886 A2 | 6/2005 |

OTHER PUBLICATIONS http://www.thefreedictionary.com, definition for "couple," accessed on Feb. 28, 2010.*

European Search Report for European Patent Application No. 07250897.1-1526 / 1834609, Jan. 12, 2009, 5 pgs.

Viano et al., "Ultrasonic Characterization of the Curing Process of Hydroxyapatite-Modified Bone Cement", *Journal of Biomedical Materials Research*, 2001, vol. 56, No. 4, pp. 593-599.

Nilsson et al., "Monitoring the Setting of Calcium-Based Bone Cements Using Pulse-Echo Ultrasound", *Journal of Materials Science: Materials in Medicine*, 2002, vol. 13, pp. 1135-1141.

Livi et al., "Dielectric Behavior at Microwave Frequencies of an Epoxy Resin During Crosslinking", *Journal of Applied Polymer Science*, 1993, vol. 50, pp. 1583-1590.

King et al., "Microwave Dynamic Dielectric Analysis of Curing Neat Resins", *Journal of Reinforced Plastics and Composites*, 1993, vol. 12, pp. 173-185.

"Tech Impedance—An Integrated Architecture for Impedance Measurement", www.sensorsmag.com, Oct. 2005, pp. 24-26.

European Search Report in corresponding European patent application (i.e. EP 06 256 545), dated Apr. 5, 2007 (6 pages).

Chinese Office Action for Chinese Patent Application No. 200710085747.1, Jan. 22, 2010, 10 pgs.

European Search Report; European Application No. 10178830.5-1526; Mar. 9, 2011; 5 pages.

* cited by examiner

APPARATUS FOR DISPENSING BONE CEMENT

CROSS-REFERENCE TO RELATED U.S. PATENT APPLICATION

Cross-reference is made to U.S. Utility patent application Ser. No. 11/095,107 entitled "Method and Apparatus for Determining the Operating Points of Bone Cement," which was filed Mar. 31, 2005 by Jason T. Sherman et al., and U.S. Utility patent application Ser. No. 11/323,871 entitled "Method and Apparatus for Determining the Operating Points of Bone Cement," which was filed Dec. 30, 2005 by Jason T. Sherman et al., the entirety of both of which is expressly incorporated herein by reference.

TECHNICAL FIELD

The present disclosure relates generally to bone cement for use in the performance of an orthopaedic procedure, and more particularly to devices for dispensing such bone cement.

BACKGROUND

Many orthopaedic procedures require the use of bone cement. Bone cement is used to, for example, secure a prosthetic implant to the patient's natural bone. Most bone cements include a self-curing resin formed from the blending of a liquid monomer or co-monomer with a powdered polymer or copolymer. A typical liquid monomer for use as the liquid component of bone cement is a monomeric methyl methacrylate. Typical powders for use as the powder component of bone cement include a methacrylate homopolymer or a methylmethacrylate-styrene copolymer. Curing of the bone cement composition occurs as the liquid and powder components polymerize and crosslink.

Bone cement is typically mixed in the surgical area just prior to its use. The curing of a bone cement composition is characterized by three operating points. The first of which is dough time. Dough time is distinguished qualitatively as the point in time where the bone cement no longer adheres to latex gloves. Dough time is measured relative to the initial mixing of the liquid and powder components. Dough time signifies the starting point of the working time of the bone cement composition. In other words, once dough time is reached, the bone cement composition has achieved a desired viscosity and flowability to allow for the delivery of the composition into the surgical or implant site.

The end-of-work time is the second operating point of a bone cement composition. It is distinguished qualitatively as the point in time where bone cement no longer adheres to itself. The end-of-work time is also measured relative to the initial mixing of the liquid and powder components. The end-of-work time signifies when the working time of the composition has ended. In other words, the end-of-work time indicates when the bone cement should no longer be used in the surgical procedure.

The third operating point of bone cement is setting time. It, too, is measured relative to the initial mixing of the liquid and powder components. The setting time signifies when the bone cement has cured sufficiently enough to maintain the prosthetic implant in the implant site (e.g., in the prepared bone).

SUMMARY

According to one aspect, an apparatus for dispensing bone cement includes a cartridge configured to contain bone cement. The bone cement may be pre-mixed or may be mixed inside the cartridge. The cartridge may be cylindrical in shape and may include a dispensing nozzle for ejecting bone cement from the cartridge. The apparatus may also include a plunger insertable into the cartridge and movable to eject bone cement within the cartridge. The cartridge and/or the plunger may be sterile. The apparatus may further include an impedance sensor coupled to the plunger. The impedance sensor may be configured to produce an output signal indicative of an impedance value of bone cement within the cartridge. The impedance sensor may be embodied as, for example, two substantially parallel plates positioned in a spaced apart configuration. The impedance sensor may be coupled to the plunger on a first side. The apparatus may also include a first connector coupled to the plunger on a second side. The first connector may be electrically coupled to the impedance sensor through the plunger. The apparatus may further include a housing configured to receive the cartridge. The apparatus may also include a rod coupled to the housing and coupleable to the plunger. The rod may be operable to move the plunger to eject bone cement from the cartridge. The rod may include a second connector configured to be mate with to the first connector. The rod may also include an internal passageway defined therein.

The apparatus may further include a processing circuit. The processing circuit may be coupled to, for example, the housing. The processing circuit may be electrically coupled to the impedance sensor. For example, the processing circuit may be electrically coupled to the impedance sensor via the first and second connectors and one or more wires positioned in the inner passageway of the rod. The processing circuit may be configured to receive the output signal from the impedance sensor and determine an impedance value of bone cement within the cartridge based on the output signal. For example, the processing circuit may be configured to determine a minimum impedance value of the bone cement. The processing circuit may include an impedance analyzer and/or a processor. The impedance analyzer may be electrically coupled to the impedance sensor and configured to determine the impedance value of bone cement within the cartridge based on the output signal. The processor may be electrically coupled to the impedance analyzer and configured to determine a minimum value of the impedance value. The processing circuit may also include a memory device and the processor may be configured to store data indicative of the impedance value determined by the impedance analyzer in the memory device.

The apparatus may yet further include a first indicator, a second indicator, and/or a third indicator coupled to the housing. The processing circuit may be configured to activate the first indicator if the dough time of bone cement within the cartridge has been achieved. The processing circuit may also be configured to activate the second indicator if the end-of-work time of bone cement within the cartridge has been reached. For example, the processing circuit may be configured to activate one of the indicators if the determined impedance value of bone cement within the cartridge is below a predetermined threshold value. The processing circuit may also be configured to activate the third indicator if the setting time of bone cement within the cartridge has been reached. For example, the processing circuit may be configured to activate the third indicator if a predetermined amount of time has elapsed since the determination of the minimum impedance value. Additionally or alternatively, the processing circuit may be configured to determine a rate of change of the impedance of the bone cement and a theoretical end-of-work time based on such rate. The processing circuit may also be configured to generate a visual "count-down" signal to notify the user of the remaining time until the end-of-work time of the bone cement will be achieved. To do so, the apparatus may include a series of light-emitting diodes (LEDs) or a display screen to provide a visual count-down to the user.

According to another aspect, an apparatus for dispensing bone cement includes a cartridge for containing bone cement. The apparatus may also include a plunger insertable into the cartridge. The plunger may be movable relative to the cartridge to eject an amount of bone cement from the cartridge. The apparatus may include an impedance sensor coupled to the plunger. The impedance sensor may be configured to produce an output signal. The apparatus may also include an indicator. The apparatus may further include a processing circuit electrically coupled to the impedance sensor and the indicator. The processing circuit may be configured to determine an impedance value of bone cement within the cartridge based on the output signal. The processing circuit may also be configured to activate the indicator based on the impedance value. For example, the processing circuit may be configured to activate the indicator if the dough time, the end-of-work time, and/or the setting time of bone cement within the cartridge has been reached. Additionally, the apparatus may include a rod detachably coupled to the plunger. The rod may be operable to move the plunger relative to the cartridge to dispense bone cement from the cartridge.

According to another aspect, an assembly for use with a bone cement cartridge includes a plunger that is insertable into the bone cement cartridge. The plunger may be movable relative to the bone cement cartridge to eject bone cement form the bone cement cartridge. The assembly may also include an impedance sensor coupled to the plunger. The impedance sensor may be embodied as a first terminal and a second terminal spaced apart from the first terminal. The first and the second terminals may be substantially parallel to each other. The impedance sensor may be configured to produce an output signal indicative of an impedance value of bone cement within the bone cement cartridge.

According to another aspect, a method for dispensing bone cement from a cartridge includes inserting a plunger having an impedance sensor coupled thereto into the cartridge. The method may also include receiving an output signal from the impedance sensor and determining an impedance value of bone cement within the cartridge based on the output signal. The method may further include generating a human-detectable signal, such as a visual or audible signal, based on the impedance value. For example, the human-detectable signal may be activated if the dough time, the end-of-work time, and/or the setting time of bone cement within the cartridge has been reached.

BRIEF DESCRIPTION OF THE DRAWINGS

The detailed description particularly refers to the following figures, in which.

DETAILED DESCRIPTION OF THE DRAWINGS

Figure 1:
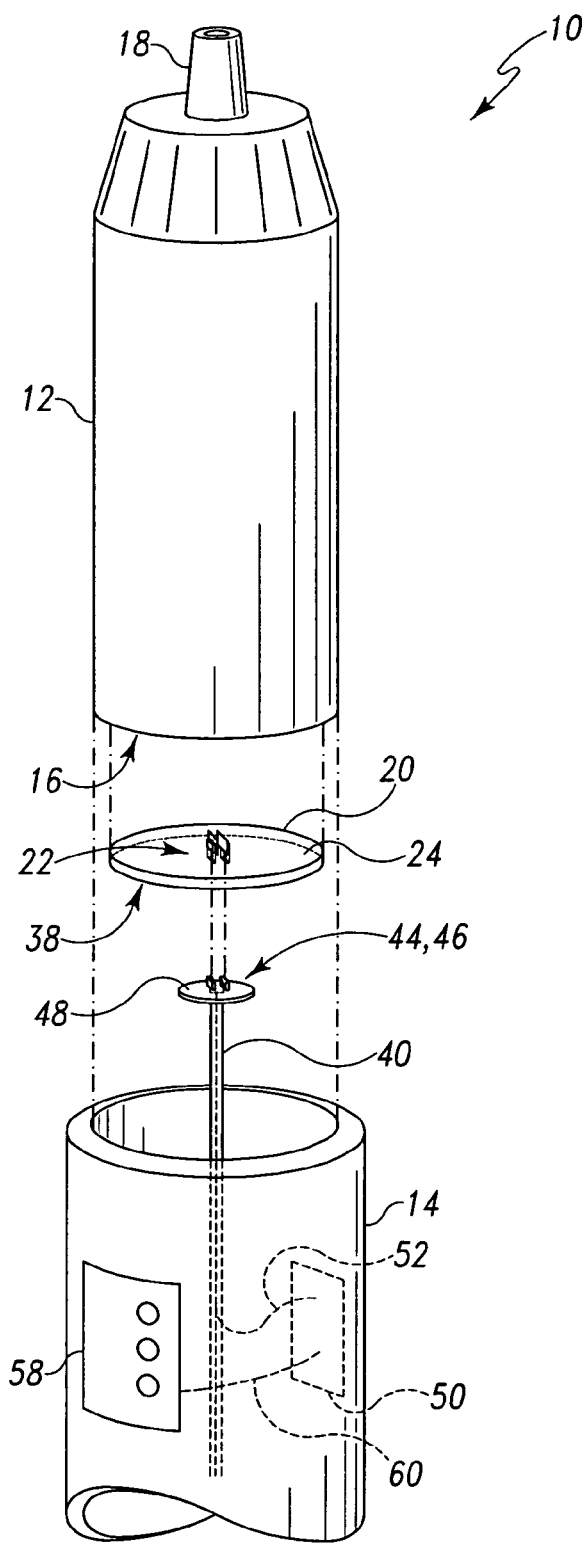
FIG. 1 is a diagramatic view of an apparatus for dispensing bone cement.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an apparatus 10 for dispensing bone cement includes a cartridge 12 and a housing 14 configured to receive the cartridge 12. The cartridge 12 includes an inner cavity 16 wherein the bone cement is placed. The cartridge 12 also includes a nozzle 18 in fluid communication with the inner cavity 16 such that bone cement may be dispensed from the inner cavity 16 via the nozzle 18. The cartridge 12 and housing 14 may be formed from any suitable material that does not adversely interact with the bone cement. For example, in some embodiments the cartridge 12 and/or housing 14 are formed from a plastic material. In some embodiments, the bone cement is mixed in a separate mixing apparatus (not shown) and subsequently placed into the inner cavity 16 of the cartridge 12. In other embodiments, the bone cement may be mixed in the inner cavity 16. For example, the liquid monomer or co-monomer and the powdered polymer or copolymer may be placed into the inner cavity 16 and mixed in-situ therein. In such embodiments, a cap (not shown) may be coupled to the nozzle 18 to restrict the inadvertent expulsion of bone cement from the inner cavity 16 during the mixing process.

The apparatus 10 also includes a plunger 20 that is shaped and sized to be insertable into the inner cavity 16 of the cartridge 12. In the illustrative embodiment, the inner cavity 16 has a substantially circular cross-section. As such, the illustrative plunger 20 also has a substantially circular shape such that the plunger 20 may be inserted into the inner cavity 16 and moved inwardly to cause an amount of the bone cement positioned in the inner cavity 16 to be dispensed via the nozzle 18. In some embodiments, a seal (not shown) is coupled to the edge of the plunger 20 to provide an improved contact between the plunger 20 and the inner walls of the cartridge 12 which define the inner cavity 16. Additionally, in some embodiments, the cartridge 12 and/or the plunger 20 may be sterile.

The apparatus 10 also includes an impedance sensor 22 coupled to a first side 24 of the plunger 20. The impedance sensor 22 is mounted to the first side 24 such that when the plunger 20 is inserted into the inner cavity 16 of the cartridge 12, the impedance sensor 22 comes into contact with the bone cement located therein. That is, the plunger 20 is inserted into the inner cavity 16 such that the first side 24 of the plunger 20 faces toward the inner cavity 16 and the nozzle 18 of the cartridge 12. As such, the plunger 20 may be formed from any material capable of supporting the impedance sensor 22 and rigid enough to compress the bone cement in the inner cavity 16 to dispense an amount of bone cement through the nozzle 18 while not adversely interacting with the bone cement. For example, in some embodiments, the plunger 20 is formed from a plastic material.

Figure 2:
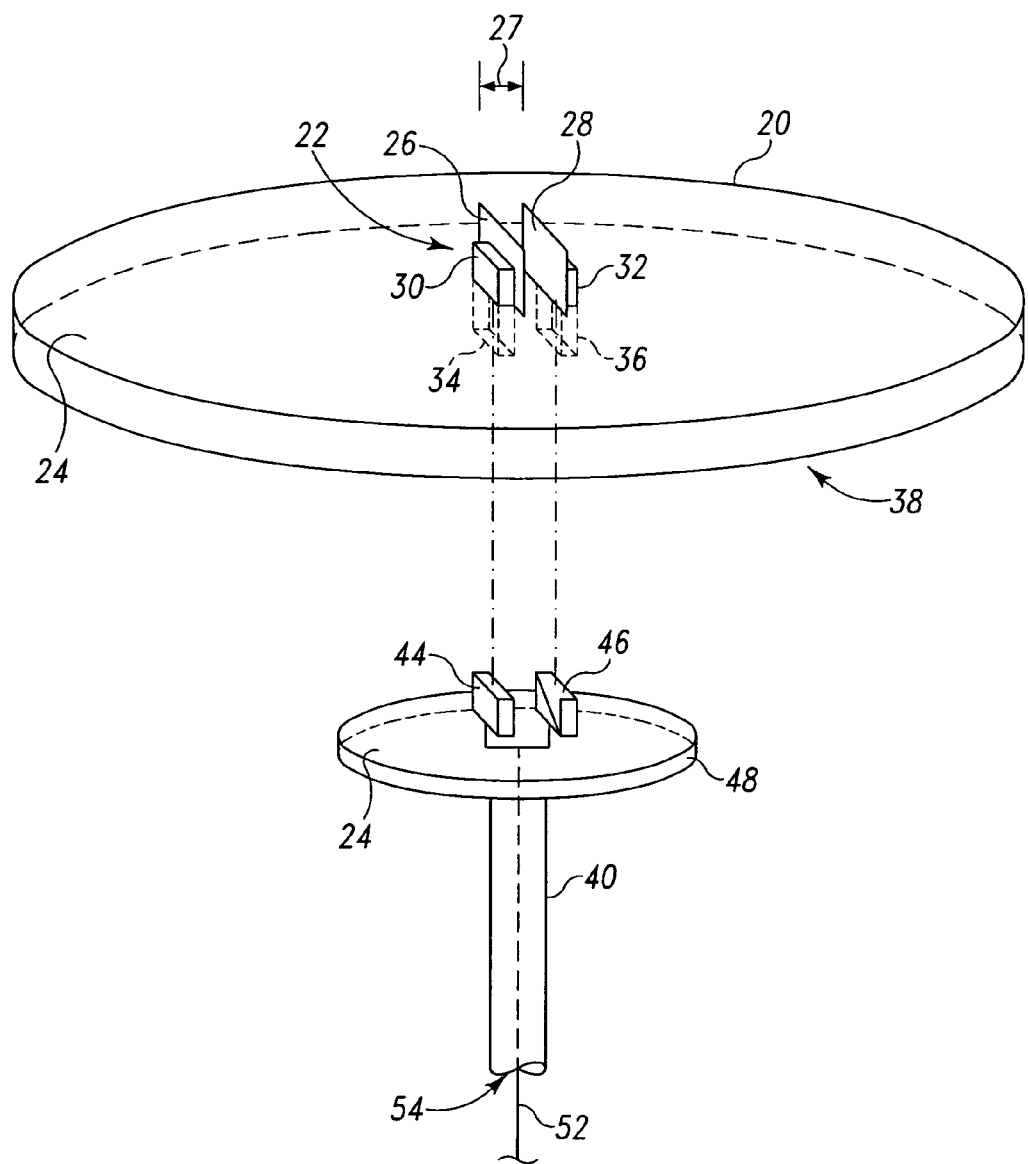
FIG. 2 is a perspective diagramatic view of a plunger assembly of the apparatus of FIG. 1.

The impedance sensor 22 may be embodied as any type of sensor capable of producing a sensor signal indicative of the impedance of the bone cement contained in the cartridge 12. As illustrated in FIG. 2, in the illustrative embodiment, the impedance sensor 22 includes a first terminal 26 and a second terminal 28. The terminals 26, 28 are illustratively embodied as metallic plates coupled to the first side 24 of the plunger 20 in substantially parallel relationship with each other. The first and second terminals 26, 28 are spaced apart a distance 27 such that when the impedance sensor 22 is contacted with bone cement located in the inner cavity 16 of the cartridge 12, a portion of the bone cement becomes positioned between the plates 26, 28. In response to the application of an appropriate voltage signal, the impedance sensor 22 produces an output signal. Based on this output signal, an impedance value of the bone cement contained in the cartridge 12 may be determined as discussed in further detail below in regard to FIGS. 4 and 5.

The first and second terminals 26, 28 of the impedance sensor 22 are coupled to the plunger 20 via a pair of connectors 30, 32, respectively. The connectors 30, 32 are electrical connectors and are in electrical communication with the first and second terminals 26, 28, respectively. The connectors 30, 32 are also electrically coupled to a pair of connectors 34, 36 (shown in shadow) coupled to the plunger 20 on a second side 38. In the illustrative embodiment, the connectors 30, 32 are electrically coupled to the connectors 34, 36, respectively, through the plunger 20. To do so, the connectors 30, 32 may be electrically coupled to the connectors 34, 36 by a number of wires, vias, or other electrical interconnections that extend through the plunger 20. Alternatively, the connectors 30 and 34 and the connectors 32 and 36 may each form a unitary connector which extends from the first side 24, through the plunger 20, to the second side 38. Regardless, the connectors 30, 32 are electrically coupled to the connectors 34, 36 such that the connectors 34, 36 located on the second side 38 of the plunger 20 are also electrically coupled to the first and second terminals 26, 28 of the impedance sensor 22. It should be appreciated that in other embodiments, other types of impedance sensors may be used. Additionally, any number and type of connectors may also be used to interconnect the impedance sensor 22 to other devices of the apparatus 10. Further, in other embodiments, other methods of securing the impedance sensor 22 to the plunger 20 may be used. For example, in some embodiments, the impedance sensor 22 may be embedded in or on the first side 24 of the plunger 20 or otherwise form an integral part thereof.

The plunger 20 is configured to be coupled to a plunger rod 40 of the housing 14. The plunger rod 40 is movable relative to housing 14. When the plunger 20 is coupled to the rod 40, the rod 40 may be moved in an outward direction relative to the housing 14 to thereby move the plunger 20 within the inner cavity 16 toward the nozzle 18 to dispense an amount of bone cement therefrom. In the illustrative embodiment, the plunger rod 40 is cylindrical in shape, however, in other embodiments, other configurations for the plunger rod 40 may be used. For example, in some embodiments, the plunger rod 40 may be substantially flat, have a rectangular shape, or have any other geometric shape that facilitates the coupling to and movement of the plunger 20. Additionally, the plunger rod 40 may be formed from any material capable of facilitating the movement of the plunger 20 in the inner cavity 16. For example, in some embodiments, the plunger rod 40 is formed from a plastic or metallic material.

As illustrated in FIG. 2, in the illustrative embodiment, the rod 40 is coupled to the plunger 20 via a pair of connectors 44, 46. The connectors 44, 46 are coupled to a substrate 48, which is mounted to a distal end of the rod 40. The substrate 48 may have any shape and be formed from any material capable of supporting the connectors 44, 46. The connectors 44, 46 are configured and orientated to mate with the connectors 34, 36, respectively, of the plunger 20 to thereby couple the plunger 20 to the plunger rod 40. To do so, the connectors 34, 36 and 44, 46 may be configured to couple with each other in any manner. For example, the connectors 34, 36 may be "female" type connectors while the connectors 44, 46 are "male" type connectors or vice-versa. Alternatively, one of the connectors 34, 36 may be a "female" type connector while the other connector 34, 36 is a "male" type connector and the connectors 44, 46 may be of corresponding "female" and "male" types. Regardless, in the illustrative embodiment, the plunger 20 is coupled to the rod 40 (i.e., to the substrate 48 of the rod 40) via the coupling of the connectors 34, 36 and 44, 46.

Referring now back to FIG. 1, the connectors 44, 46 are also electrically coupled to a processing circuit 50. Illustratively, the connectors 44, 46 are electrically coupled to the processing circuit 50 via a number of interconnects 52 positioned in an inner passageway 54 of the plunger rod 40 (see FIG. 2). The interconnects 52 may be embodied as any type of interconnects capable of providing electrical communication between the impedance sensor 22 and the processing circuit 50 such as, for example, wires, cables, fiber optic cables, or the like. The interconnects 52 are electrically coupled to the connectors 44, 46 through the substrate 48 and extend downwardly therefrom through the inner passageway 54. The interconnects 52 exit the inner passageway 54 via a hole 56 (see FIG. 3) or other access means and are electrically coupled to the processing circuit 50. In this way, when the plunger 50 is coupled to the plunger rod 40, the impedance sensor 22 is electrically coupled to the processing circuit 50 via the connectors 30, 32, 34, 36, 44, 46 and the wires 52.

The processing circuit 50 is also coupled to an indicator panel 58 located on the housing 14 via a number of interconnects 60. Similar to the interconnects 52, the interconnects 60 may be embodied as any type of interconnects capable of providing electrical communication between the processing circuit 50 and the indicator panel 58 such as, for example, wires, cables, fiber optic cables, or the like.

Figure 3:
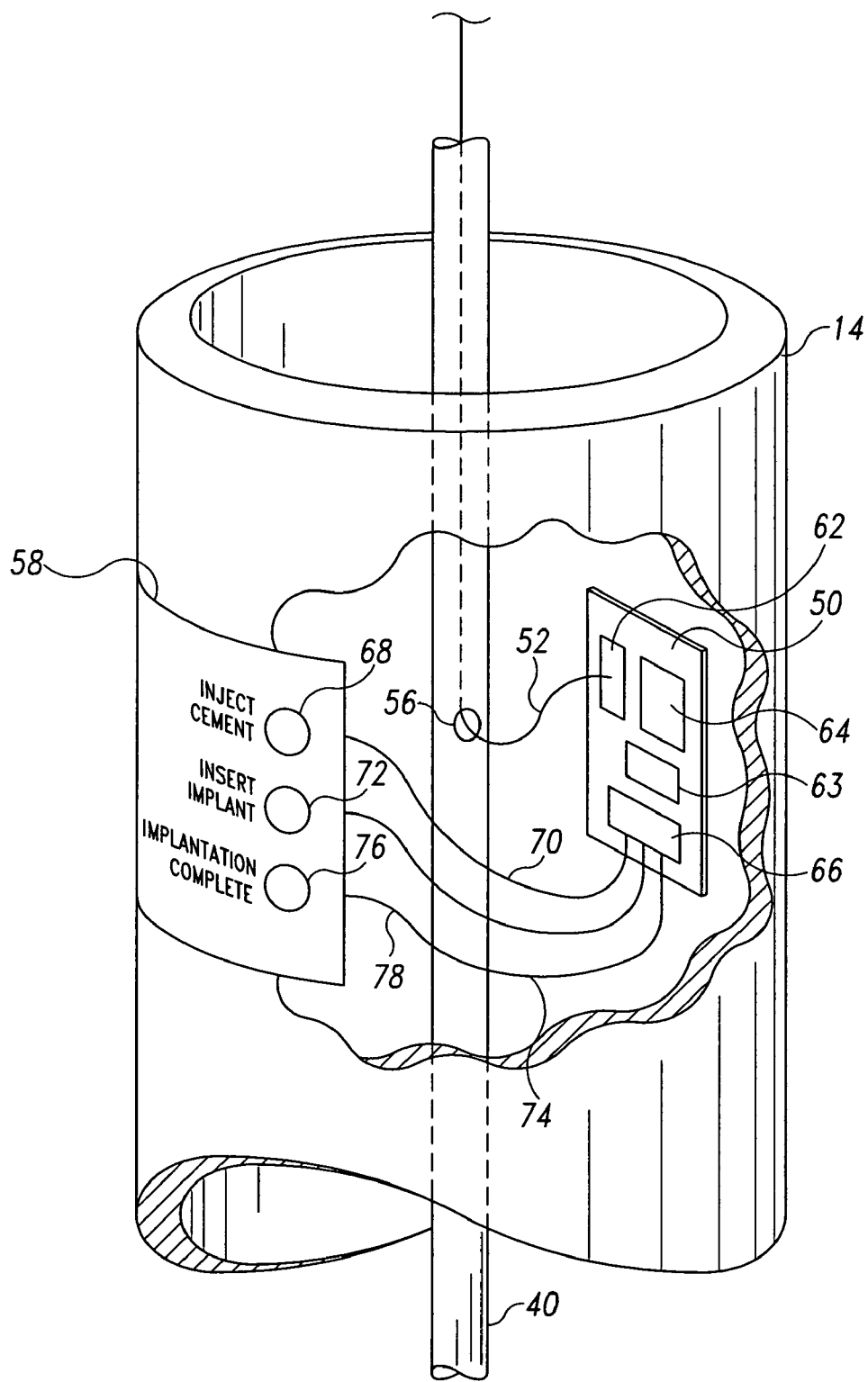
FIG. 3 is a diagrammatic view of a housing of the apparatus of FIG. 1 having a portion cut away for clarity of description.

Referring now to FIG. 3, in one embodiment, the processing circuit 50 includes an impedance analyzer 62, a memory device 63, a processor 64 electrically coupled to the impedance analyzer 62 and the memory device 63, and a display driver circuit 66 electrically coupled to the processor 64. The impedance analyzer 62 is electrically coupled to the impedance sensor 22 via the interconnects 52. The display driver circuit 66 is electrically coupled to a first indicator 68 of the indicator panel 58 via interconnects 70. The display driver circuit 66 is also electrically coupled to a second indicator 72 of the indicator panel 58 via interconnects 74. The display driver circuit 66 is further electrically coupled to a third indicator 76 of the indicator panel 58 via interconnects 78. The interconnects 70, 74, 78 may be any type of interconnects capable of electrically coupling the display driver circuit 66 of the processing circuit 50 to the indicators 68, 72, 76. Illustratively, the indicators 68, 72, 76 are light emitting diodes (LEDs), however, in other embodiments, the indicators 68, 72, 76 may be embodied as any type of visual indicator capable of providing a visual notification to a user of the apparatus 10. Additionally, although the illustrative embodiment of FIG. 3 includes three indicators 68, 72, 76, any number of indicators may be used in other embodiments. Further, in some embodiments, the indicator panel 58 includes a display screen, such as a liquid crystal display (LCD) screen, instead of or in addition to the indicators 68,

72, 76. In such embodiments, the display driver circuit 66 is configured to control the display screen to display information to the user of the apparatus 10.

Although illustrated in FIGS. 1 and 3 as being coupled to an internal side wall of the housing 14, it should be appreciated that the processing circuit 50 may be coupled to the housing 14 in any location wherein the processing circuit 50 is also capable of being electrically coupled to the impedance sensor 22 and the indicator panel 58. For example, in some embodiments, the processing circuit 50 may be mounted in a handle of the housing 14.

Figure 4:
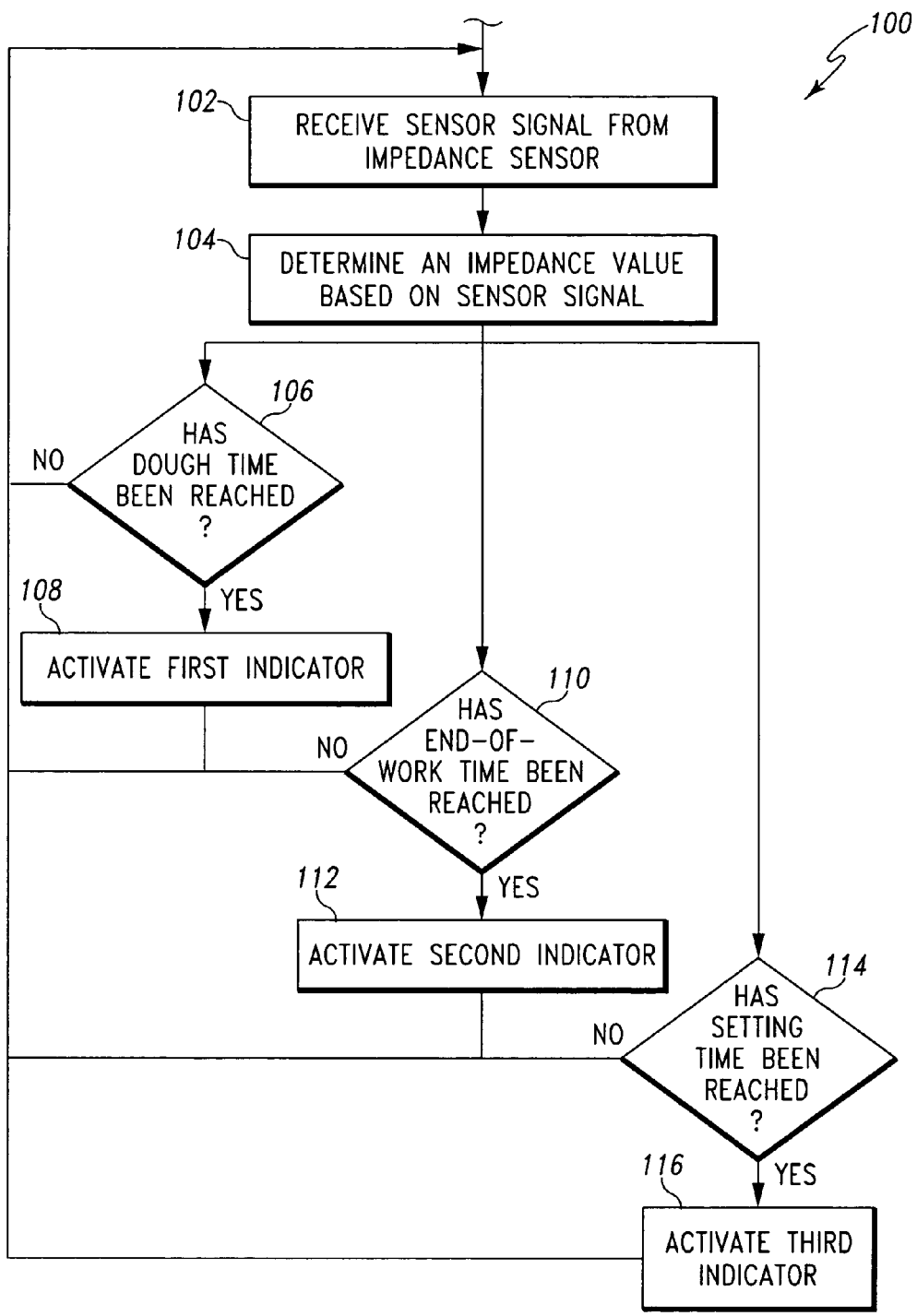
FIG. 4 is a flowchart of an algorithm for determining conditions of bone cement, which may be executed by a processing circuit of the apparatus of FIG. 1.

In operation, the processing circuit 50 is configured to determine the condition of the bone cement located in the inner cavity 16 of the cartridge 12. To do so, in some embodiments, the processing circuit 50 may be configured to execute an algorithm 100 for determining the condition of the bone cement. As illustrated in FIG. 4, the algorithm 100 beings with a process step 102 in which an output signal is received from the impedance sensor 22. The output signal is received by the impedance analyzer 62 of the processing circuit 50. In some embodiments, the impedance analyzer 62 is configured to periodically sample the output signal produced by the impedance sensor 22. In process step 104, an impedance value of the bone cement is determined based on the output signal received in the process step 102. To do so, the impedance analyzer 62 is configured to calculate the impedance value using the output signal. For example, in some embodiments, the impedance analyzer 62 is configured to correlate a voltage and/or current value of the output signal to an impedance value.

Once an impedance value has been determined in process step 104, the algorithm 100 advances to process steps 106, 110, and 114. It should be appreciated that the process steps 106, 110, 114 may be executed contemporaneously with each other. In process step 106, the processing circuit 50 determines if the dough time of the bone cement located in the cartridge 12 has been reached. To do so, the processing circuit 50 may be configured to determine if a predetermined amount of time has lapsed since the bone cement has been mixed. For example, the processing circuit 50 may be configured to wait a predetermined amount of time after the cartridge 12 has been coupled to the housing 14. The processing circuit 50 may determine that the cartridge 12 has been so coupled based on the output signal produced by the impedance sensor 22. In other embodiments, the processing circuit 50 may be configured to determine if the dough time of the bone cement has been reached based on the impedance value of the bone cement. For example, the processing circuit 50 may be configured to determine that the dough time of the bone cement has been reached if a predetermined impedance value is achieved. Regardless, if the dough time of the bone cement located in the cartridge 12 has been reached, the processing circuit 50 is configured to activate the first indicator 68 in process step 108. By activating the first indicator 68, the processing circuit 50 may notify the user of the apparatus 10 that the bone cement may be injected into, for example, a bone of a patient. The first indicator 68 may be activated continually, periodically, or for a predetermined amount of time. If, however, the dough time has not been reached, the algorithm 100 loops back to process step 102 wherein the output signal from the impedance sensor 22 is received by the impedance analyzer 62 of the processing circuit 50.

Figure 5:
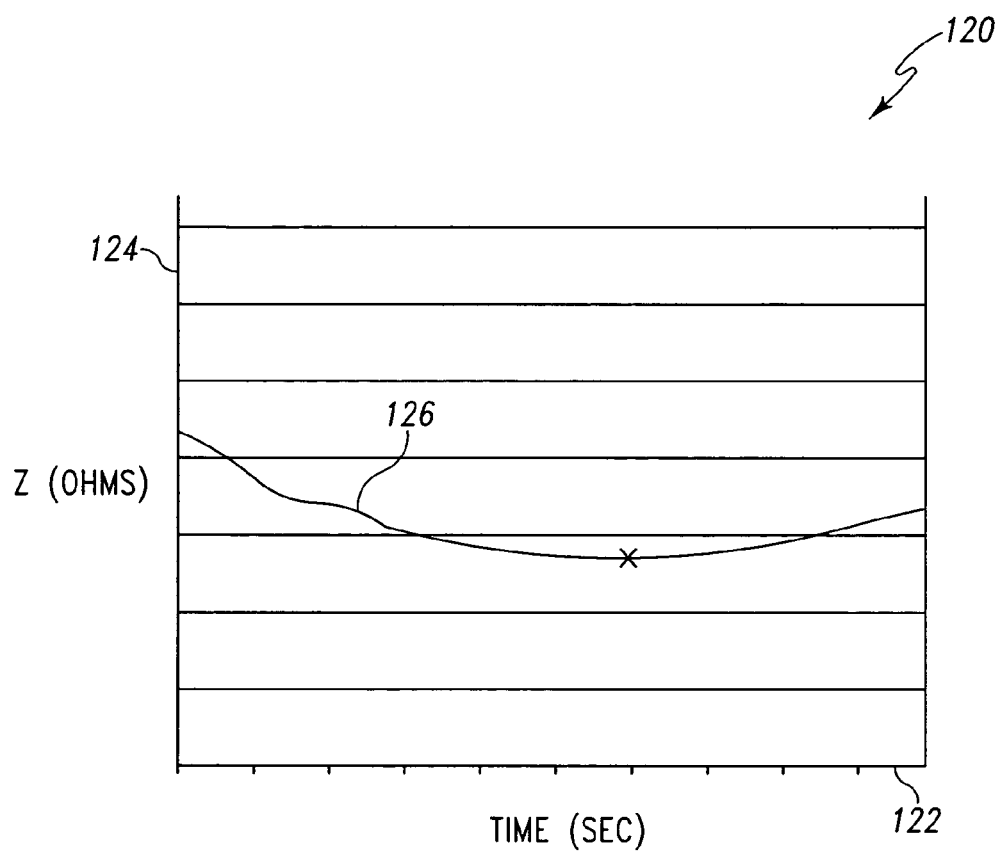
FIG. 5 is a graph showing a plot of a theoretical relationship between the impedance of a bone cement composition and time.
Figure 6:
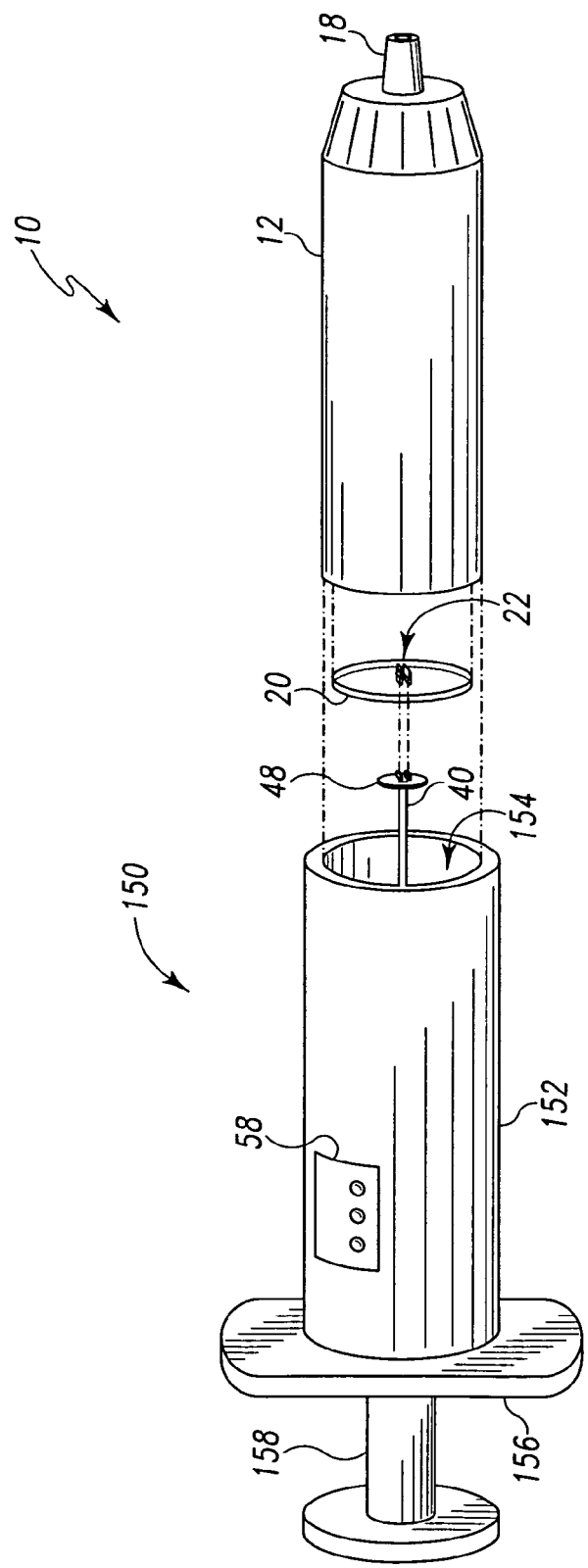
FIG. 6 is a diagrammatic view of one embodiment of the apparatus of FIG. 1.

In process step 110, the processing circuit 50 determines if the end-of-work time of the bone cement located in the cartridge 12 has been reached. To do so, in some embodiments, the processing circuit 50 (e.g., the processor 64) may be configured to determine if a minimum impedance value of the bone cement has been achieved. As the bone cement cures, the impedance value of the bone cement decreases to a minimum value and subsequently begins to increase until the bone cement is fully cured. For example, as illustrated in FIG. 5, a graph 120 of the impedance value of an amount of typical bone cement as it cures over time is illustrated. The graph 120 includes an abscissa axis 122 graduated in units of time and an ordinate axis 124 graduated in units of impedance (ohms). A plot line 126 illustrates the impedance value of the bone cement over time. As shown in FIG. 6, as time increases, the impedance value of the bone cement reaches a minimum value designated by an "X" on the graph 120. After the impedance value of the bone cement has reached the minimum value, the bone cement impedance begins to increase again. In some embodiments, the minimum impedance value of the bone cement correlates to the end-of-work time. Accordingly, by determining the minimum impedance value of the bone cement, the end-of-work time may be determined.

To determine if a minimum impedance value of the bone cement located in the inner cavity 16 of the cartridge 12 has been achieved, in some embodiments, the processor 64 may be configured to store impedance values, or data indicative thereof, determined by the impedance analyzer 62 in the memory device 63. The processor 64 may then replace the stored impedance values with new impedance values if the new impedance value is less than the stored impedance value. Once the processor 64 determines that the new impedance value is greater than the stored impedance value, the processor 64 may be configured to acknowledge that a minimum impedance value of the bone cement has been achieved and determine that the end-of-work time of the bone cement located in the cartridge 12 has been reached. It should be appreciated that the minimum impedance value so determined may be a local or global minimum impedance value.

Alternatively or additionally, the processing circuit 50 may be configured to determine that a minimum impedance value of the bone cement has been achieved if the impedance value determined by the impedance analyzer 62 falls below a predetermined minimum threshold value. In other embodiments, other methods for determining if the end-of-work time of the bone cement has been reached may be used. For example, in some embodiments, the end-of-work time of the bone cement may be determined based on the phase angle of the impedance value of the bone cement, inflection points of the impedance graph, and/or time values. Additional description of techniques for determining if the end-of-work time for the bone cement has been achieved are disclosed in copending, commonly-owned U.S. Utility patent application Ser. No. 11/095,107 entitled "Method and Apparatus for Determining the Operating Points of Bone Cement," which was filed Mar. 31, 2005 by Jason T. Sherman et al. and in copending, commnonly-owned U.S. Utility patent application Ser. No. 11/323/871 entitled "Method and Apparatus for Determining the Operating Points of Bone Cement," which was filed Dec. 30, 2005 by Jason T. Sherman et al., the entirety of both of which is expressly incorporated herein by reference.

If the end-of-work time of the bone cement located in the cartridge 12 has been reached, the processing circuit 50 is configured to activate the second indicator 72 in process step 112. By activating the second indicator 72, the processing circuit 50 may notify the user of the apparatus 10 that the implant should be inserted into the relevant bone or other area wherein the bone cement has been injected. The second indicator 72 may be activated continually, periodically, or only for a predetermined amount of time. If, however, the end-of-work time has not been reached, the algorithm 100 loops back to process step 102 wherein the sensor signal from the impedance sensor 22 is received by the impedance analyzer 62 of the processing circuit 50.

Additionally or alternatively, in other embodiments, the processing circuit 50 is configured to determine a rate of change of the impedance value of the bone cement based on the impedance values received from the impedance sensor 22. The processing circuit 50 may subsequently determine a theoretical end-of-work time of the bone cement based on rate of change of the impedance of the bone cement. In such embodiments, the processing circuit 50 may be configured to provide a "count-down" indicator to a user of the apparatus 10 to notify the user of the time remaining until the end-of-work time of the bone cement is reached. For example, the apparatus 10 may include a series of light-emitting diodes (LEDs) that are activated by the processing circuit 50 in a sequential order to provide a visual count-down indicator to the user. Alternatively, the apparatus 10 may include a display, such as a liquid crystal display (LCD), that is operated by the processing circuit 50 to provide a numerical, visual count-down indicator to the user.

In process step 114, the processing circuit 50 determines if the setting time of the bone cement located in the cartridge 12 has been reached. To do so, in some embodiments, the processing circuit 50 may be configured to determine if a predetermined amount of time has lapsed since the determination of a minimum impedance value of the bone cement. The processing circuit 50 may be configured to determine that the setting time has been reached once the predetermined amount of time after the minimum impedance value has been achieved. However, in other embodiments, other methods of determining that the setting time of the bone cement has been reached may be used. Additional description of techniques for determining if the setting time for the bone cement has been achieved are also disclosed in copending, commonly-owned U.S. Utility patent application Ser. No. 11/095,107 entitled "Method and Apparatus for Determining the Operating Points of Bone Cement," which was filed Mar. 31, 2005 by Jason T. Sherman et al. and in copending, commonly-owned U.S. Utility patent application Ser. No. 11/323/871 entitled "Method and Apparatus for Determining the Operating Points of Bone Cement," which was filed Dec. 30, 2005 by Jason T. Sherman et al., the entirety of both of which is expressly incorporated herein by reference.

If the end-of-work time of the bone cement located in the cartridge 12 has been reached, the processing circuit 50 is configured to activate the third indicator 76 in process step 116. By activating the third indicator 76, the processing circuit 50 may notify the user of the apparatus 10 that the bone cement has cured and that the implantation process is complete. The third indicator 76 may be activated continually, periodically, or only for a predetermined amount of time. If, however, the end-of-work time has not been reached, the algorithm 100 loops back to process step 102 wherein the sensor signal from the impedance sensor 22 is received by the impedance analyzer 62 of the processing circuit 50.

Figure 7:
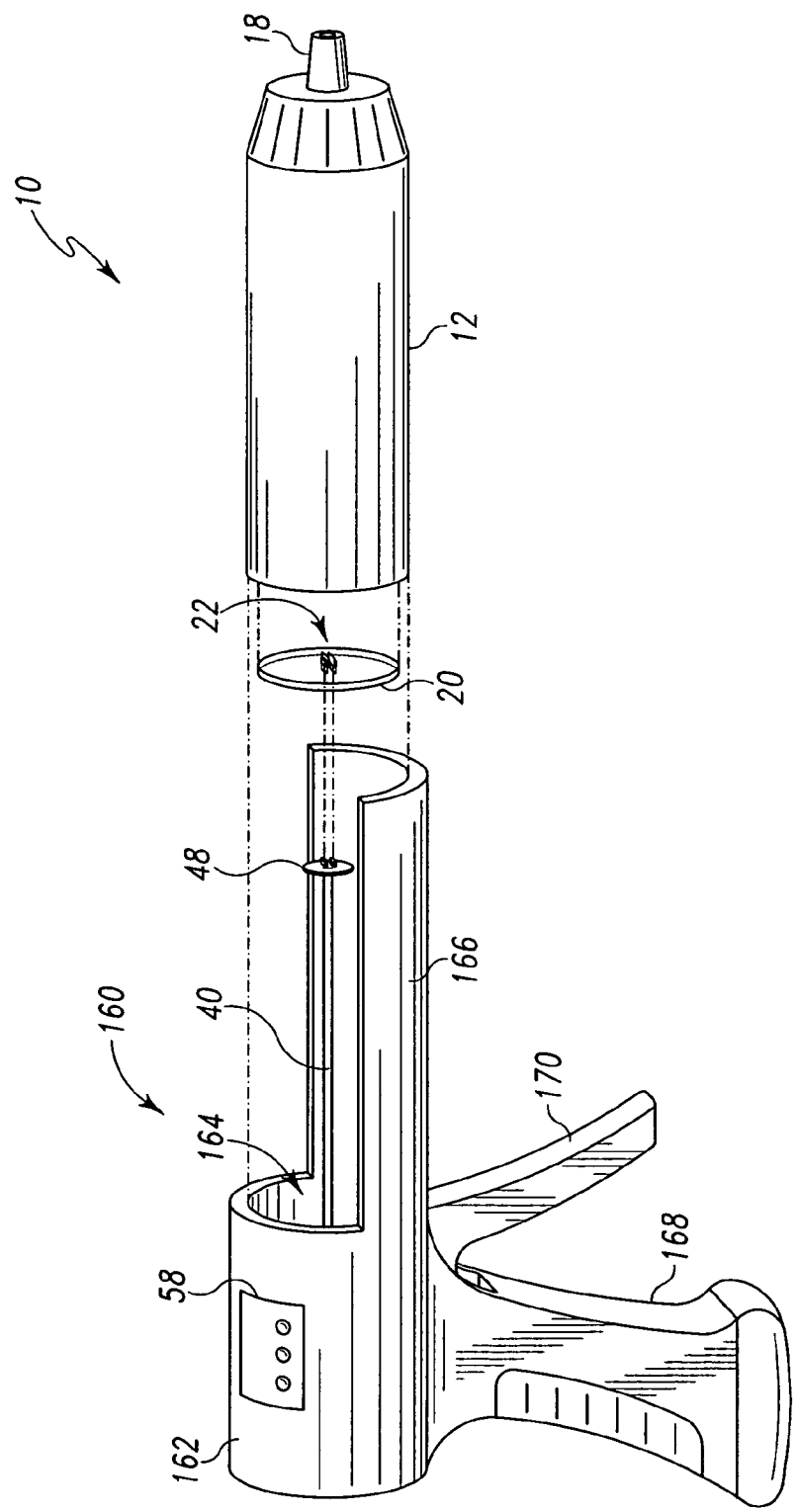
FIG. 7 is a diagrammatic view of another embodiment of the apparatus of FIG. 1.

Referring now to FIGS. 6 and 7, the housing 14 may be embodied as any type of housing capable of receiving the cartridge 12. As discussed above in regard to FIG. 1, the illustrative cartridge 12 is substantially cylindrical in shape and, as such, the housing 14 is configured to receive a cylindrically shaped cartridge. However, in other embodiments, the cartridge 12 may have any shape and the housing 14 may be configured to receive a cartridge having such shape.

In some embodiments, as illustrated in FIG. 6, the housing 14 is embodied as a syringe 150. The syringe 150 includes a housing 152 having a cylindrical aperture 154 configured to receive the cartridge 12 or portion thereof. Once the cartridge 12 is inserted into the cylindrical aperture 154, the cartridge 12 may be secured to the housing 152 via connectors, couplings, a twist lock, of other securing means. The plunger rod 40 extends from the aperture 154 such that the plunger rod 40 may be coupled to the plunger 20 of the cartridge 12 when the cartridge 12 is coupled to syringe 150. The syringe 150 also includes finger supports 156 and a thumb depressor 158, which is movable with respect to the housing 152. The plunger rod 40 is coupled to the thumb depress 158. In use, a user of the apparatus 10 may move the thumb depress 158 by pressing down thereon, which causes the rod 40 to move in an outward direction with respect to the housing 152. Because the plunger rod 40 is coupled to the plunger 20, the plunger rod 40 causes the plunger 20 to be moved inwardly with respect to the cartridge 12 and thereby dispense an amount of bone cement located in the inner cavity 16 of the cartridge 12 via the nozzle 18. Once the cartridge 12 has been used to dispense the desired amount of bone cement, the cartridge 12 may be removed from the syringe 150 and disposed of. When the syringe 150 is used again, a new cartridge 12 may be loaded in or otherwise coupled to the syringe 150 and used in the manner discussed above to dispense a desired amount of bone cement.

Referring now to FIG. 7, in another embodiment, the housing 14 is embodied as a dispensing gun 160. The dispensing gun 160 includes a housing 162 having a cylindrical aperture 154 configured to receive a portion of the cartridge 12. The housing 162 also includes a support member 166 configured to support the cartridge 12. In the illustrative embodiment, the support member 166 is shaped as a half-cylinder such that the outer wall of the cartridge 12 may be supported by the inner wall of the support member 166. The cartridge 12 may be secured to the housing 162 via connectors, couplings, a twist lock, of other securing means. The plunger rod 40 extends from the aperture 164 such that the plunger rod 40 may be coupled to the plunger 20 of the cartridge 12 when the cartridge 12 is coupled to dispensing gun 160. The dispensing gun 160 also includes a handle 168 and a trigger 170, which is movable with respect to the housing 152. The plunger rod 40 is movably coupled to the trigger 170. In use, a user of the apparatus 10 may actuate the trigger 170 by depressing the trigger 170 toward the handle 168, which causes the rod 40 to move in an outward direction with respect to the housing 162. Because the plunger rod 40 is coupled to the plunger 20, the plunger rod 40 causes the plunger 20 to be moved inwardly with respect to the cartridge 12 and thereby dispense an amount of bone cement located in the inner cavity 16 of the cartridge 12 via the nozzle 18. Once the cartridge 12 has been used to dispense the desired amount of bone cement, the cartridge 12 may be removed from the dispensing gun 160 and disposed of. When the dispensing gun 160 is used again, a new cartridge 12 may be loaded in or otherwise coupled to the dispensing gun 160 and used in the manner discussed above to dispense a desired amount of bone cement.

It should be appreciated that although the apparatus 10 has been described above as a manually operated device, the apparatus 10 may be powered in some embodiments. In such embodiments, the apparatus 10 may include an internal power source such as an internal electrical power source (e.g., a battery) or may receive power from an external power source such as via an Alternating Current (AC) outlet. Additionally or alternatively, the apparatus 10 may receive power from an external mechanical power source such as a rotary power source typically available in orthopaedic surgical operating rooms. Regardless, the power source is operably coupled to the rod 40 via appropriate power transmission devices such as motors, gears, linkages, cams, crank arms, or the like. As such, a user may operate the apparatus 10 by "activating" the thumb depress 158, the trigger 170, or the like to cause an amount of bone cement to be ejected from the cartridge 12. In response to the activation of the thumb depress 158, trigger 170, or the like, the power source and power transmission devices cooperate to cause the rod 40 to be moved so as to eject the bone cement. The force required by the user to eject the bone cement may be reduced because of the cooperation of the power source and power transmission devices. In addition, the apparatus 10 may be configured to dispense or eject a predetermined amount of bone cement for each "activation" of the thumb depress 158, the trigger 170, or the like. Additionally or alternatively, the amount of bone cement ejected from the cartridge 12 may be determined based on, for example, the length of time which the thumb depress 148, trigger 170, or the like is held in a depressed position.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus and method described herein. It will be noted that alternative embodiments of the apparatus and method of the present disclosure may not include all of the features described yet still benefit from at least some of the advantages of such features. Those of ordinary skill in the art may readily devise their own implementations of the apparatus and method that incorporate one or more of the features of the present invention and fall within the spirit and scope of the present disclosure as defined by the appended claims.

The invention claimed is:

1. An apparatus for dispensing bone cement, the apparatus comprising:
   a housing;
   a cartridge having a first end positioned in the housing, a second end extending outwardly therefrom, and a nozzle formed at the second end;
   a plunger positioned in the cartridge and movable to eject bone cement from the cartridge through the nozzle, the plunger having a first side facing the nozzle;
   an impedance sensor mounted to the first side of the plunger and configured to produce an output signal indicative of an impedance value of bone cement within the cartridge;
   a rod operable to move the plunger relative to the housing, the rod having an internal passageway defined therein; and
   a processing circuit secured to the housing, the processing circuit being electrically coupled to the impedance sensor by a wire positioned in the internal passageway of the rod and configured to receive the output signal from the impedance sensor.

2. The apparatus of claim 1, wherein the impedance sensor comprises:
   a first metallic plate; and
   a second metallic plate spaced apart from the first metallic plate such that the first and second metallic plates are substantially parallel to each other.

3. The apparatus of claim 1, wherein the cartridge and the plunger are sterile.

4. The apparatus of claim 1, further comprising a first connector coupled to the plunger on a second side, wherein:
   the impedance sensor is electrically coupled to the first connector.

5. The apparatus of claim 4, wherein the rod includes a second connector configured to mate with the first connector.

6. The apparatus of claim 1, further comprising a first indicator electrically coupled to the processing circuit, wherein the processing circuit is configured to activate the first indicator if the impedance value of bone cement within the cartridge is below a predetermined threshold value.

7. The apparatus of claim 6, further comprising a second indicator electrically coupled to the processing circuit, wherein the processing circuit is configured to activate the second indicator if a predetermined amount of time has elapsed since the activation of the first indicator.

8. The apparatus of claim 1, further comprising a first indicator, a second indicator, and a third indicator each electrically coupled to the processing circuit, wherein the processing circuit is configured to:
   (i) activate the first indicator if a dough time of bone cement within the cartridge has been achieved,
   (ii) activate the second indicator if an end-of-work time of bone cement within the cartridge has been reached, and
   (iii) activate the third indicator if a setting time of bone cement within the cartridge has been reached.

9. The apparatus of claim 1, wherein the processing circuit is configured to store data values indicative of the impedance value of bone cement within the cartridge.

10. An apparatus for dispensing bone cement, the apparatus comprising:
    a housing;
    a cartridge having a first end positioned in the housing, a second end extending outwardly therefrom, and a nozzle formed at the second end;
    a plunger positioned in the first end of the cartridge and movable relative to the cartridge to eject an amount of bone cement from the cartridge through the nozzle, the plunger having a first side facing the nozzle;
    an impedance sensor mounted to the first side of the plunger and configured to produce an output signal;
    an indicator located on the housing; and
    a processing circuit electrically coupled to the impedance sensor and the indicator, wherein the processing circuit is configured to:
    (i) determine an impedance value of bone cement within the cartridge based on the output signal, and
    (ii) activate the indicator based on the impedance value.

11. The apparatus of claim 10, wherein the processing circuit is configured to activate the indicator if a dough time of bone cement within the cartridge has been reached.

12. The apparatus of claim 10, wherein the processing circuit is configured to activate the indicator if an end-of-work time of bone cement within the cartridge has been reached.

13. The apparatus of claim 10, wherein the processing circuit is configured to activate the indicator if a setting time of bone cement within the cartridge has been reached.

14. The apparatus of claim 10, further comprising a rod detachably coupled to the plunger and operable to move the plunger relative to the cartridge.

15. A method for dispensing bone cement from a cartridge, the method comprising:
    ejecting bone cement from an apparatus, the apparatus comprising:
    a housing, a cartridge having a first end positioned in the housing, a second end extending outwardly therefrom, and a nozzle formed at the second end, a plunger positioned in the cartridge and movable to eject bone cement from the cartridge through the nozzle, the plunger having a first side facing the nozzle, an impedance sensor mounted to the first side of the plunger and configured to produce an output signal indicative of an impedance value of bone cement within the cartridge, a rod operable to move the plunger relative to the housing, the rod having an internal passageway defined therein, and a processing circuit secured to the housing, the processing circuit being electrically coupled to the impedance sensor by a wire positioned in the internal passageway of the rod and configured to receive the output signal from the impedance sensor;

receiving an output signal from the impedance sensor;

determining an impedance value of bone cement within the cartridge based on the output signal; and generating a human-detectable signal based on the impedance value.

16. The method of claim 15, wherein the generating step comprises activating a first indicator if the impedance value of bone cement within the cartridge is below a predetermined threshold value.

17. The method of claim 16, further comprising activating a second indicator if a predetermined amount of time has elapsed since the activation of the first indicator.

18. The method of claim 15, wherein the generating step comprises generating a human-detectable signal if a dough time of bone cement within the cartridge has been reached.

19. The method of claim 15, wherein the generating step comprises generating a human-detectable signal if an end-of-work time of bone cement within the cartridge has been reached.

20. The method of claim 15, wherein the generating step comprises generating a human-detectable signal if a setting time of bone cement within the cartridge has been reached.

21. An apparatus for dispensing bone cement, the apparatus comprising:

a cartridge having a nozzle;

a plunger insertable into the cartridge and movable to eject bone cement from the cartridge through the nozzle, the plunger having a first side facing the nozzle;

a first connector coupled to the plunger;

an impedance sensor mounted to the first side of the plunger and configured to produce an output signal indicative of an impedance value of bone cement within the cartridge;

a housing configured to receive the cartridge;

a rod operable to move the plunger relative to the housing; and a second connector coupled to the rod and configured to mate with the first connector to removably couple the rod to the plunger.

22. The apparatus of claim 21, wherein the cartridge and the plunger are sterile.

23. The apparatus of claim 21, wherein:

the first connector is coupled to a second side of the plunger, and the impedance sensor is electrically coupled to the first connector.

24. The apparatus of claim 21, further comprising a processing circuit electrically coupled to the second connector.

* * * * *